United States Patent
Voronin et al.

(10) Patent No.: US 8,575,351 B2
(45) Date of Patent: Nov. 5, 2013

(54) ACTIVE METABOLITE OF A THROMBIN RECEPTOR ANTAGONIST

(75) Inventors: Kimberly Nguyen Voronin, Hillsborough, NJ (US); Natalia A. Penner, Cambridge, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/376,093

(22) PCT Filed: Jun. 2, 2010

(86) PCT No.: PCT/US2010/036984
§ 371 (c)(1),
(2), (4) Date: Apr. 19, 2012

(87) PCT Pub. No.: WO2010/141525
PCT Pub. Date: Dec. 9, 2010

(65) Prior Publication Data
US 2012/0214845 A1    Aug. 23, 2012

Related U.S. Application Data

(60) Provisional application No. 61/184,147, filed on Jun. 4, 2009.

(51) Int. Cl.
*C07D 401/00* (2006.01)
*A61K 31/24* (2006.01)

(52) U.S. Cl.
USPC ........................ 546/268.1; 514/337

(58) Field of Classification Search
None
See application file for complete search history.

(56) References Cited

U.S. PATENT DOCUMENTS

| | | | |
|---|---|---|---|
| 6,057,337 A | 5/2000 | Kobayashi et al. |
| 6,063,847 A | 5/2000 | Chackalamannil et al. |
| 6,326,380 B1 | 12/2001 | Chackalamannil et al. |
| 6,645,987 B2 | 11/2003 | Chackalamannil et al. |
| 7,115,632 B1 | 10/2006 | Bedell et al. |
| 7,235,567 B2 | 6/2007 | Wu |
| 7,304,078 B2 | 12/2007 | Chackalamannil et al. |
| 2003/0203927 A1 | 10/2003 | Chackalamannil et al. |
| 2003/0216437 A1 | 11/2003 | Chackalamannil et al. |
| 2004/0152736 A1 | 8/2004 | Chackalamannil et al. |
| 2004/0192753 A1 | 9/2004 | Chackalamannil et al. |
| 2006/0058287 A1 | 3/2006 | Axten et al. |
| 2007/0202140 A1 | 8/2007 | Veltri et al. |
| 2008/0026050 A1 | 1/2008 | Gupta et al. |
| 2008/0031943 A1 | 2/2008 | Gupta et al. |
| 2008/0152712 A1 | 6/2008 | Monteith et al. |

FOREIGN PATENT DOCUMENTS

| | | |
|---|---|---|
| WO | 03/089428 | 10/2003 |
| WO | WO03089428 A1 | 10/2003 |
| WO | WO 03089428 A1 * | 10/2003 |
| WO | 2005/046688 | 5/2005 |
| WO | WO 2008042422 A2 * | 4/2008 |
| WO | WO 2008060372 A2 * | 5/2008 |

OTHER PUBLICATIONS

Lewis, R., ed. Hawley's Condensed Chemical Dictionary, 15th edition, NY John Wiley & Sons, 2007, p. 711.*
Search Report (PCT/ISA/210) Mailing Date: Oct. 11, 2010.
ROC (Taiwan) Patent Application No. 099117984 Search Report (1page), 2006.

* cited by examiner

*Primary Examiner* — Janet Andres
*Assistant Examiner* — Heidi Reese
(74) *Attorney, Agent, or Firm* — Mark W. Russell; Catherine D. Fitch

(57) ABSTRACT

Disclosed herein is an active metabolite ("M20") of a molecule that is useful as a thrombin receptor antagonist: Also disclosed are formulations of this compound, synthetic routes to this compound, and methods of treating a variety of cardiovascular conditions, including acute coronary syndrome and peripheral arterial disease, and of effecting secondary prevention, by orally administering the active metabolilte.

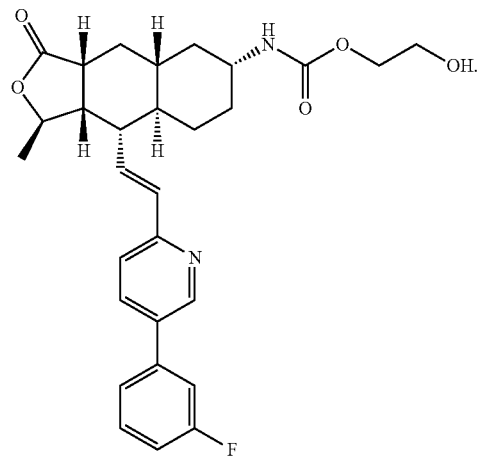

SCH 2046273

7 Claims, 9 Drawing Sheets

ACTIVE METABOLITE OF A THROMBIN RECEPTOR ANTAGONIST

RELATED APPLICATIONS

The present application claims the benefit of U.S. provisional application no. 61/184,147; filed Jun. 4, 2009; which is herein incorporated by reference in its entirety.

FIELD OF THE INVENTION

The invention relates to an active metabolite of a thrombin receptor antagonist, and pharmaceutical compositions and therapeutic methods of using either.

BACKGROUND

Schering Corp. is developing a thrombin receptor antagonist ("TRA") for use in a variety of cardiovascular applications, including treatment of acute coronary syndrome ("ACS") and secondary prevention. The active pharmaceutical ingredient ("API"), SCH 530348, has completed phase I and II clinical trials, and is currently in phase III trials. The development of an understanding of the metabolism of SCH 530348 is both a desirable progression in the science and a necessary step in the commercialization of this thrombin receptor antagonist.

Thrombin is known to have a variety of activities in different cell types and thrombin receptors are known to be present in such cell types as human platelets, vascular smooth muscle cells, endothelial cells and fibroblasts. It is therefore possible that thrombin receptor antagonists, also known as protease activated receptor (PAR) antagonists, will be useful in the treatment of thrombotic, inflammatory, atherosclerotic and fibroproliferative disorders, as well as other disorders in which thrombin and its receptor play a pathological role.

U.S. Pat. No. 7,304,078 discloses a genus of compounds, including a specific thrombin receptor antagonist compound identified as Example 2, herein identified as SCH 530348. SCH 530348 has the following structure:

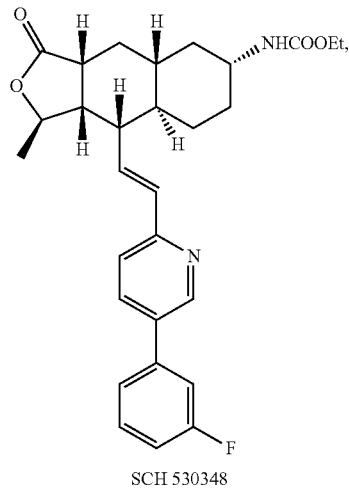

SCH 530348 and the following chemical formula: Ethyl[(1R,3aR,4aR,6R,8aR,9S,9aS)-9-[(E)-2-[5-(3-fluorophenyl)-2-pyridinyl]ethenyl]dodecahydro-1-methyl-3-oxonaphtho[2,3-c]furan-6-yl] carbamate. SCH 530348 exhibits good thrombin receptor antagonist activity (potency) and selectivity, and is currently in development by Schering Corp. Co-pending U.S. patent application Ser. No. 10/705,282, herein incorporated by reference, discloses a variety of indications and combination formulations for thrombin receptor antagonists including SCH 530348. A preferred crystalline form of the bisulfate salt of SCH 530348 is disclosed in U.S. Pat. No. 7,235,567. U.S. patent application Ser. Nos. 11/771,571; 11/771,520; and 11,860,165 disclose capsule formulations, tablet formulations and lyophilized formulations (respectively) of SCH 530348, and methods of treating various conditions by administering same.

The use of a small subset of thrombin receptor antagonists to treat a variety of conditions and diseases is disclosed in U.S. publication no. 04/0192753. The prevention of complications associated with cardiopulmonary bypass surgery by administration of a thrombin receptor antagonist is taught in U.S. application Ser. No. 11/613,450. Methods of preventing cardiac events after percutaneous intervention ("PCI," e.g., angioplasty, stent introduction) are disclosed in U.S. application Ser. No. 12/051,504. Substituted thrombin receptor antagonists are disclosed in U.S. Pat. Nos. 6,063,847; 6,326,380; and 6,645,987 and U.S. publication nos. 03/0203927; 04/0216437A1; 04/0152736; and 03/0216437. All of the herein cited references are incorporated in their entirety.

It would be beneficial to identify any active metabolites of SCH 530348 that persist in the body after dosing. The invention seeks to provide these and other benefits, which will become apparent as the description progresses.

SUMMARY OF THE INVENTION

In some embodiments, the present invention is directed to a compound of the following formula:

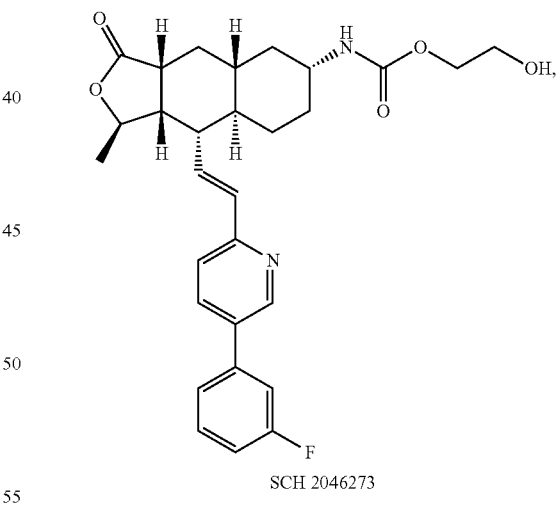

SCH 2046273 or a pharmaceutically acceptable isomer, salt or hydrate thereof.

In some embodiments, the compound SCH 2046273 is in the form of the free base.

In some embodiments, the compound SCH 2046273 is in the form of a pharmaceutically acceptable salt.

In some embodiments, the compound SCH 2046273 is in the form of a hydrate.

In some embodiments, the compound SCH 2046273 is an isolated and purified form of the compound, or of a pharmaceutically acceptable isomer, salt or hydrate thereof.

In some embodiments, the invention is directed to a pharmaceutical composition comprising an effective amount of the compound SCH 2046273, or a pharmaceutically acceptable isomer, salt or hydrate thereof, and a pharmaceutically acceptable carrier.

In some embodiments, the pharmaceutical composition further comprises one or more additional cardiovascular agents.

In some embodiments, the cardiovascular agent is selected from the group consisting of aspirin, clopidogrel, and prasugrel, and the pharmaceutically acceptable isomers, salts and hydrates thereof.

In some embodiments, the present invention is directed to a method of treating a cardiovascular condition comprising administering to a mammal in need of such treatment an effective amount of the compound SCH 2046273, or a pharmaceutically acceptable isomer, salt or hydrate thereof.

In some embodiments, the cardiovascular condition is selected from the group consisting of acute coronary syndrome, peripheral arterial disease, thrombosis, atherosclerosis, restenosis, hypertension, angina pectoris, arrhythmia, heart failure, myocardial infarction, glomerulonephritis, thrombotic stroke, thromboembolic stroke, and cerebral ischemia.

In some embodiments, the cardiovascular condition is acute coronary syndrome.

In some embodiments, the cardiovascular condition is peripheral arterial disease.

In some embodiments, the present invention is directed to a method of preventing a condition associated with coronary arterial bypass graft surgery comprising administering an effective amount of the compound SCH 2046273, or a pharmaceutically acceptable isomer, salt or hydrate thereof, to a subject of said surgery.

In some embodiments, the condition associated with coronary arterial bypass graft surgery is selected from the group consisting of: bleeding; thrombotic vascular events such as thrombosis, restenosis; vein graft failure; artery graft failure; atherosclerosis, angina pectoris; myocardial ischemia; acute coronary syndrome myocardial infarction; heart failure; arrhythmia; hypertension; transient ischemic attack; cerebral function impairment; thromboembolic stroke; cerebral ischemia; cerebral infarction; thrombophlebitis; deep vein thrombosis; and, peripheral vascular disease.

In some embodiments, the present invention is directed to a method of preventing a major cardiac event in a patient who has undergone percutaneous coronary intervention and is in need of such prevention comprising administering a therapeutically effective amount of the compound SCH 2046273, or a pharmaceutically acceptable isomer, salt or hydrate thereof to the patient.

In some embodiments, the major cardiac event is a myocardial infarction, urgent revascularization, or ischemia requiring hospitalization.

In some embodiments, the present invention is directed to a method of treating a patient in need of secondary prevention by orally administering to said patient a therapeutically effective amount of the compound SCH 2046273, or a pharmaceutically acceptable isomer, salt or hydrate thereof to the patient.

In some embodiments, the present invention is directed to a method of inhibiting TRAP-induced platelet aggregation in a patient in need thereof comprising administering a therapeutically effective amount of the compound SCH 2046273, or a pharmaceutically acceptable isomer, salt or hydrate thereof to the patient.

In some embodiments, the present invention is directed to a process for preparing Compound 2

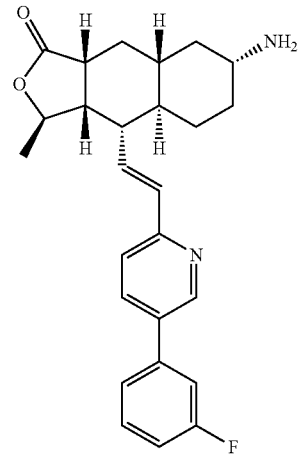

2 comprising the steps of:
a) adding a first mixture of conc. HCl and AcOH to SCH 530348-W (1)

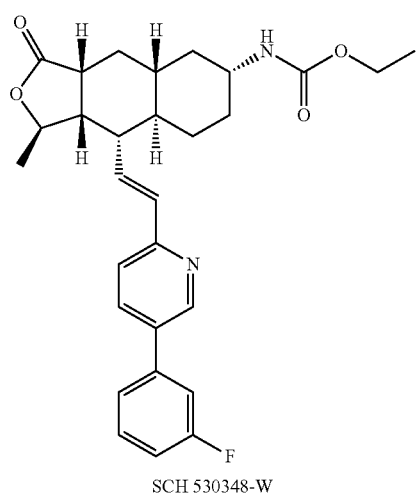

SCH 530348-W

1 to form a second mixture;
b) heating said second mixture to a temperature of between about 100 and about 140° C. for a period of between about 10 and about 30 hours;
c) cooling said second mixture to room temperature to form a crude oil;
d) adding a saturated $NaHCO_3$ solution to the crude oil to form a third mixture with a pH of between about 6 and about 10;
e) partitioning said third mixture with $CH_2Cl_2$;
f) extracting an organic layer from the third mixture with $CH_2Cl_2$; and,
g) drying said extracted organic layer over $Na_2SO_4$ to form a white foam (2).

In some embodiments, the first mixture comprises HCl and AcOH present in a ratio of between about 1.8 and about 2.2.

In some embodiments, the second mixture is heated to a temperature of between about 115 and about 120° C.

In some embodiments, the pH of said third mixture is brought to between about 7.5 and about 8.5.

In some embodiments, the present invention is directed to a process for preparing Compound 4

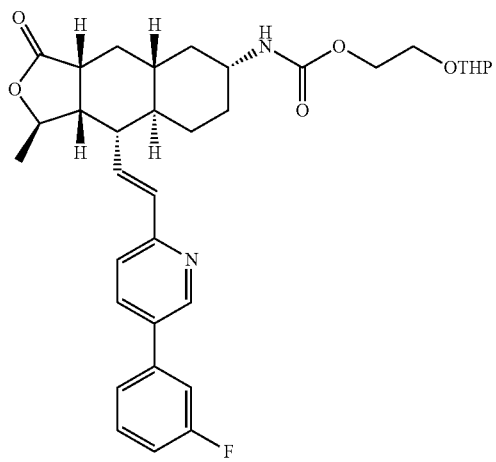

comprising the steps of:
a) adding triphosgene to a mixture of Compound (2) in CH$_2$Cl$_2$ and sat. NaHCO$_3$;
b) removing the organic layer;
c) extracting the aqueous layer with CH$_2$Cl$_2$;
d) drying the combined organic layers over Na$_2$SO$_4$ to form an isocyanate intermediate as a clear foam;
e) dissolving the clear foam in anhydrous CH$_2$Cl$_2$ and adding copper(I) chloride;
f) adding 2-(tetrahydro-2H-pyran-2-yloxy)ethanol; and,
g) washing with water and drying over Na$_2$SO$_4$ to form Compound 4.

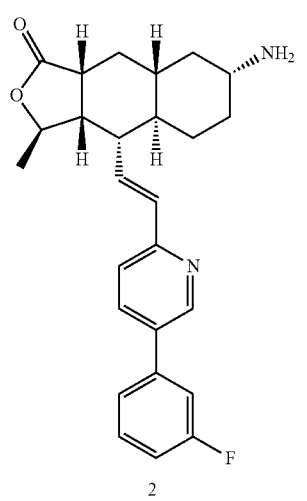

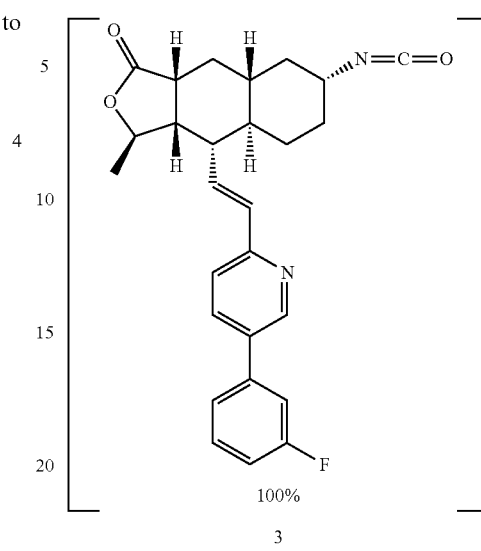

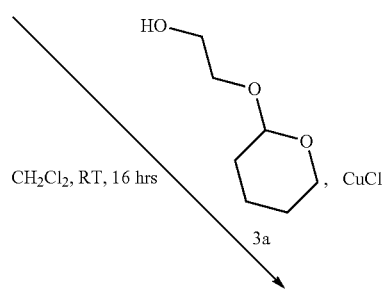

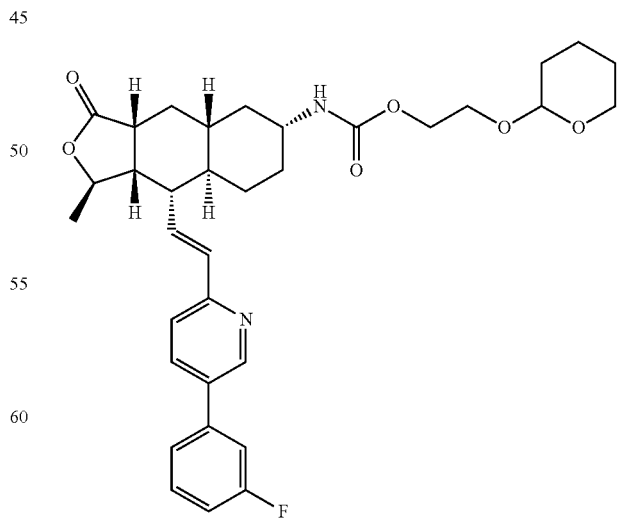

In some embodiments, the present invention is directed to a process for preparing SCH 2046273 (5)

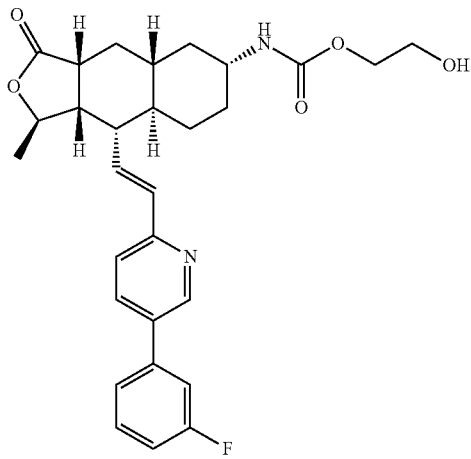 [SMILES: C[C@H]1OC(=O)[C@@H]2C[C@@H]3C[C@H](NC(=O)OCCO)CC[C@H]3[C@H](/C=C/c3ccc(-c4cccc(F)c4)cn3)[C@H]12]

comprising the steps of:
a) dissolving Compound (4) in absolute EtOH;

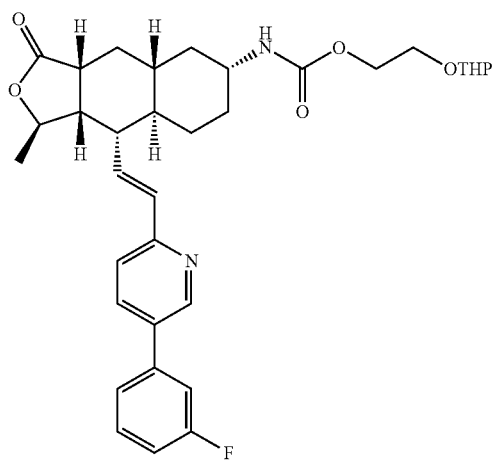

b) adding to said solution pyridinium p-toluenesulfonate;
c) heating said solution to a temperature between about 50 and about 60° C.; and,
d) evaporating to dryness to form a crude clear oil.

A further understanding of the invention will be had from the following description and claims.

DESCRIPTION OF THE INVENTION

Figure 1:
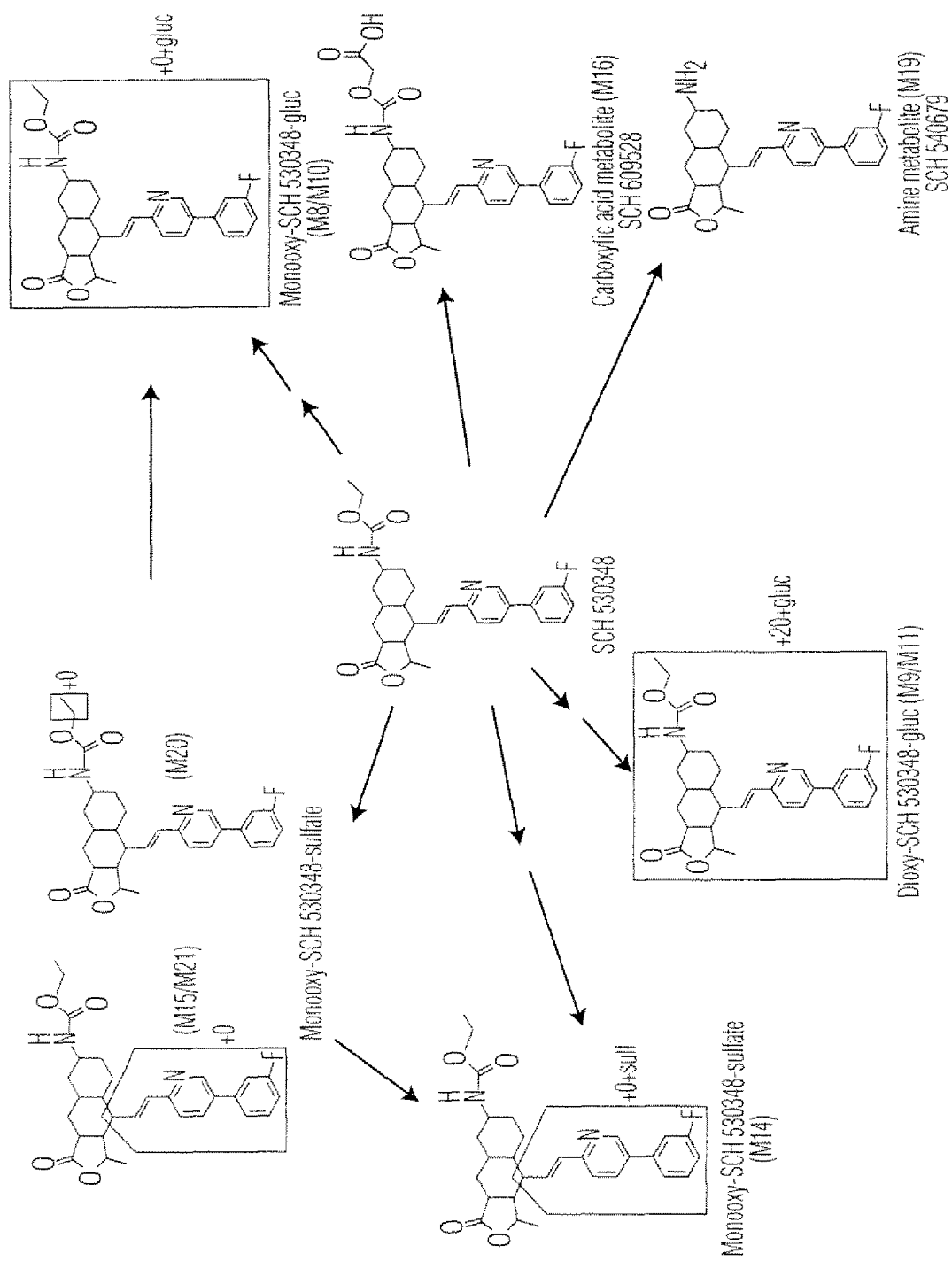
FIG. 1 illustrates the metabolites detected in plasma and urine following 20- and 40-mg single oral administrations of SCH 530348 to male human subjects.

Phase I clinical studies were designed to evaluate the pharmacokinetics of SCH 530348 in healthy subjects after rising single and multiple doses. The studies included a randomized, evaluator-blind, placebo-controlled, rising single dose ("RSD") study and a rising multiple dose ("RMD") study of orally administered SCH 530348 in healthy subjects. The designs of both the RSD and RMD studies are provided in Table 1.

TABLE 1

|  | Rising Single Dose Study | Rising Multiple Dose Study |
| --- | --- | --- |
| Treatment | 0.25 mg, 1 mg, 5 mg, 10 mg, 20 mg, 40 mg or placebo | 1 mg, 3 mg, 5 mg or placebo, once daily for 28 days |
| Subjects | Healthy male subjects, n = 6/dose (2:1 randomization) | Healthy male and female subjects; n = 8/dose (2:1 randomization) |
| Analytical Assay | LC-MS/MS (LLOQ = 0.1 ng/ml) | |
| Metabolic Analysis | Qualitative, Identification | |

The studies resulted in the identification of at least 15 distinct metabolites whose structures were inferred. A description of the studies and their results are as follows.

The Rising Single Dose Study

In the single-dose study, 50 healthy males were enrolled into 6 sequential cohorts and randomized to receive in ascending dose manner placebo (n=2-3/group) or oral SCH 530348 (0.25, 1, 5, 10, 20 and 40 mg; n=5-6/group). The objective of this study was to qualitatively assess SCH 530348 metabolites in selected plasma and urine samples following administration of a single oral dose (20 mg or 40 mg, Groups 5 and 6, respectively) of SCH 530348 to healthy male human subjects. Plasma samples from subjects receiving 20 mg and 40 mg of SCH 530348 or placebo were profiled using liquid chromatography-mass spectrometry ("LC-MS"). Only urine samples from 40 mg dose group were profiled. Corresponding plasma and urine LC-MS profiles from the drug- and placebo-dosed subjects were compared to distinguish the drug-derived components from the endogenous material. Next, metabolites were further characterized using liquid chromatography-tandem mass spectrometry ("LC-MS/MS") methods. Pathways involved in metabolism of SCH 530348 in humans were proposed.

The samples were analyzed using LC-MS System B comprised of TSQ Quantum (Thermo Electron Corp., San Jose, Calif.) operating in a positive electrospray ionization mode, HPLC module Alliance 2695 (Waters, Corp., Milford, Mass.), and flow scintillation analyzer 500TR Series (PerkinElmer Life and Analytical Sciences, Inc., Boston, Mass.).

The clinical phase of the study was conducted at Pharma Bio-Research Group B.V. (Zuidlaren, The Netherlands). Selected plasma and urine samples from Group 5 (20 mg dose and placebo) and Group 6 (40 mg dose and placebo) were shipped and received frozen at Schering-Plough Research Institute ("SPRI"). The samples were stored at −20±10° C. until processing and analysis for metabolites.

Plasma samples from subjects dosed with SCH 530348 or with placebo, in the and 40 mg dose groups, were pooled as summarized in the following table.

TABLE 2

| Time Point (hr) (Dose Type) | Subject No. | Plasma Volume Pooled from Each Subject[a] (mL) | Total Volume of Pooled Plasma (mL) | Volume of Extracted Plasma (mL) |
|---|---|---|---|---|
| 40-mg dose (Group 6) | | | | |
| 1 (Placebo) | 601 | 1.3 | 4.0 | 4.0 |
| | 605 | 1.3 | | |
| | 607 | 1.4 | | |
| 1 (SCH 530348) | 602 | 1.3 | 6.8 | 6.8 |
| | 603 | 1.2 | | |
| | 604 | 1.4 | | |
| | 606 | 1.5 | | |
| | 608 | 1.2 | | |
| 6 (Placebo) | 601 | 1.3 | 4.1 | 4.1 |
| | 605 | 1.3 | | |
| | 607 | 1.5 | | |
| 6 (SCH 530348) | 602 | 1.6 | 7.5 | 7.5 |
| | 603 | 1.7 | | |
| | 604 | 1.2 | | |
| | 606 | 1.6 | | |
| | 608 | 1.4 | | |
| 20-mg dose (Group 5) | | | | |
| 1 (Placebo) | 502 | 3.05 | 6.3 | 6.3 |
| | 506 | 3.25 | | |
| 1 (SCH 530348) | 501 | 2.4 | 12.5 | 12.5 |
| | 503 | 2.7 | | |
| | 504 | 2.4 | | |
| | 505 | 2.5 | | |
| | 507 | 2.5 | | |
| 6 (Placebo) | 502 | 3.2 | 4.8 | 4.8 |
| | 506 | 1.6 | | |
| 6 (SCH 530348) | 501 | 2.7 | 14.8 | 14.8 |
| | 503 | 2.9 | | |
| | 504 | 2.9 | | |
| | 505 | 2.9 | | |
| | 507 | 3.4 | | |

[a]The total volume of primary and back-up plasma samples (for subjects in Group 5 only)

To determine extraction efficiency, all available pre-dose plasma from subjects dosed with SCH 530348 (40-mg dose group) was also pooled across subjects. A 2.0 mL aliquot of plasma was spiked with 10 µL of a system suitability mixture ("SSM") [SCH 530348 and $^{14}$C-SCH 530348 (combined concentration 40 ng/µL, 5000 DPM/µL), SCH 540679 (40 ng/µL), and SCH 609528 (40 ng/µL)] and processed by solvent extraction with protein precipitation. After extracting once with three volumes of acetonitrile, the supernatant was concentrated and reconstituted in dimethylsulfoxide (~50% of final sample volume) followed by the addition of 1/1 mixture of mobile phases A and B. Following centrifugation, a sample aliquot was analyzed by liquid chromatography-mass spectrometry/flow scintillation analysis (LC-MS/FSA). The extraction procedure resulted in 96.4% recovery of the added radiocarbon.

A similar procedure was used to process all plasma samples from the drug- or placebo-administered subjects (20- and 40-mg dose groups), and an aliquot of each reconstituted extract was injected for LC-MS analysis. Targeted LC-MS/MS analysis to confirm the presence of metabolites and characterize their structures was also performed.

Urine samples collected during the first 24-hr period post 40-mg dose were pooled across all SCH 530348-dosed subjects (n=5) and across placebo subjects (n=3). Five milliliters of urine (20% of available urine) were pooled from each subject.

To determine the extraction efficiency, 10% of available pre-dose urine from subjects to be dosed with SCH 530348 was also pooled across the subjects. An aliquot (ca. 3.15 mL) was spiked with 15 µL of SSM and extracted by solid-phase extraction. The urine sample was loaded onto a conditioned Sep-Pak Vac tC18 (Waters Corp.) cartridge and washed with water. Drug-derived material was then eluted with methanol. This extraction procedure achieved quantitative (110%) recovery of spiked radiolabeled drug. Extracted sample was concentrated, reconstituted, and analyzed by LC-MS/FSA as described for plasma samples. A similar procedure was used to process 0-24-hr urine samples from the drug- or placebo-administered subjects in Group 6. To obtain reasonable mass spectral signal, approximately 3 mL of urine from subjects dosed with 40 mg of SCH 530348 was extracted for single LC-MS analysis. Structures of metabolites detected in urine by LC-MS were further characterized by targeted LC-MS/MS analysis.

The structure of the administered drug and proposed structures of metabolites detected in this study are provided in FIG. 1. All metabolites detected and characterized in plasma and urine extracts following a single oral administration of 20 and 40 mg of SCH 530348 to healthy male volunteers are listed in Table 3.

TABLE 3

| Metabolite Label | Name | m/z[a] (Th) | Rt[b] (min) | Matrix |
|---|---|---|---|---|
| M8 | Monooxy-SCH 530348-gluc | 685 | 18.6 | Urine |
| M9 | Dioxy-SCH 530348-gluc | 701 | 18.9 | Urine |
| M10 | Monooxy-SCH 530348-gluc | 685 | 19.1 | Urine |
| M11 | Dioxy-SCH 530348-gluc | 701 | 19.1 | Urine |
| M14 | Monooxy-SCH 530348-sulfate | 589 | 22.7 | Urine |
| M15 | Monooxy-SCH 530348 | 509 | 22.8 | Urine |
| M16 | Carboxylic acid metabolite (SCH 609528) [[[[(1R,3aR,4aR,6R,8aR,9S,9aS)-9-[(E)-2-[5-(3-fluorophenyl)-2-pyridinyl]ethenyl]dodecahydro-1-methyl-3-oxonaphtho[2,3-c]furan-6-yl]amino]carbonyl]oxy]acetic acid | 523 | 22.9 | Urine |
| M19 | Amine metabolite (SCH 540679) (3R,3aS,4S,4aR,7R,8aR,9aR)-7-amino-4-[(E)-2-[5-(3-fluorophenyl)-2-pyridinyl]ethenyl]-decahydro-3-methylnaphtho[2,3-c]furan-1(3H)-one | 421 | 30.3 | Plasma, Urine |
| M20 | Monooxy-SCH 530348 | 509 | 30.3 | Plasma |
| M21 | Monooxy-SCH 530348 | 509 | 31.8 | Plasma |

[a]m/z of protonated SCH 530348 is 493 Th
[b]Retention time was obtained from LC-MS/MS experiments.

Assuming the extraction recovery and the LC-MS response of SCH 530348 and its metabolites are similar, unchanged drug was the primary circulating component during the first 6-hr period following a single 20- or 40-mg administration of SCH 530348 to humans. Trace amounts of amine (M19, SCH 540679, m/z 421 Th) and two monooxy (M20 and M21, m/z 509 Th) metabolites were also detected in plasma. A third monooxy metabolite of SCH 530348 (M15, m/z 509 Th) was detected in urine. While SCH 530348 was not detected, a sulfate conjugate of monooxy-SCH 530348 (M14, m/z 589 Th), glucuronic acid conjugates of mono- and dioxy-SCH 530348 (M8/M10 at m/z 685 Th, M9/M11 at m/z 701 Th), a carboxylic acid metabolite (M16, SCH 609528, m/z 523 Th), and an amine metabolite (M19) were detected in urine at minor to trace levels. These data suggest low clearance of drug-related components in urine.

As summarized in FIG. 1, the biotransformation pathways for SCH 530348 in human plasma and urine appear to involve carbamate hydrolysis and oxidation at various positions followed by glucuronidation and sulfation.

The following conclusions can be drawn from the rising single dose study:

First, SCH 530348 was the only major circulating drug-related component detected in 1- and 6-hr plasma following administration of a single SCH 530348 dose (20 and 40 mg) to healthy male volunteers.

Second, the low mass spectral signal observed for metabolites in urine and no response for parent drug suggested limited clearance of SCH 530348 by the renal route.

Third, SCH 530348 metabolites detected in human plasma and urine were formed through carbamate hydrolysis and oxidation at various positions followed by glucuronidation and sulfation.

Rising Multiple Dose Study

In the multiple-dose study, 36 healthy subjects were enrolled into 3 sequential cohorts and randomized to receive in ascending-dose manner placebo (n=4/group) or oral SCH 530348 (1, 3, and 5 mg OD in the morning for 28 days, n=8/group). A fourth cohort in the same study (n=12) was randomized to receive a single loading dose of SCH 530348, 10 mg (n=6) or 20 mg (n=6) on Day 1, followed by maintenance doses of 1 mg daily for 6 days. Measured and derived pharmacokinetic parameters were used to assess the pharmacokinetic profile. The design of the RMD study is summarized in Table 1 above. The objective of this study was to profile and/or characterize metabolites in human plasma by LC-MS following 5 mg once-daily oral administration of SCH 530348 (Group 3) to healthy subjects for 28 days. Selected plasma samples (Days 1, 14 and 28) from subjects receiving 5 mg of SCH 530348 or placebo daily were pooled across subjects within each treatment and then profiled using liquid chromatography-mass spectrometry (LC-MS). Corresponding plasma LC-MS profiles from the drug- and placebo-dosed subjects were compared to distinguish the drug-derived components from the endogenous material. Next, metabolites were further characterized using liquid chromatography-tandem mass spectrometry (LC-MS/MS) methods. Pathways involved in metabolism of SCH 530348 in humans were proposed.

All samples were analyzed using LC-MS System B comprised of a TSQ Quantum (Thermo Electron Corp., San Jose, Calif.) operating in a positive electrospray ionization mode, an Alliance 2695 HPLC module (Waters, Corp., Milford, Mass.), and a 500TR Series flow scintillation analyzer (PerkinElmer Life and Analytical Sciences, Inc., Boston, Mass.). The clinical phase of the study was conducted at Pharma Bio-Research Group B.V. (Zuidlaren, The Netherlands). Selected plasma samples from Group 3 (5-mg dose and placebo) were shipped and received frozen at SPR1. The samples were stored at −20±10° C. until processing and analysis for metabolites.

All available plasma from subjects dosed with SCH 530348 (n=8) or with placebo (n=4) was pooled as summarized in the following table:

TABLE 4

| Dose Type | Subject No. | Total Volume of Pooled and Extracted Plasma (mL) | | | | | | | |
|---|---|---|---|---|---|---|---|---|---|
| | | Day 1 | | Day 14 | | | Day 28 | | |
| | | 2 | 6 | 0 | 2 | 6 | 0 | 2 | 6 |
| SCH 530348 | 302 | 16.4 | 18.8 | 21.1 | 19.7 | 21.2 | 20.7 | 22.2 | 22.4 |
| | 303 | | | | | | | | |
| | 304 | | | | | | | | |
| | 306 | | | | | | | | |
| | 307 | | | | | | | | |
| | 308 | | | | | | | | |
| | 310 | | | | | | | | |
| | 312 | | | | | | | | |
| Placebo | 301 | 9.6 | 9.5 | 9.9 | 9.3 | 10.3 | 10.2 | 10.1 | 10.8 |
| | 305 | | | | | | | | |
| | 309 | | | | | | | | |
| | 311 | | | | | | | | |

Extraction efficiency of parent drug from human plasma has been previously determined in the rising single dose study by spiking a system suitability mixture [SSM, SCH 530348 and $^{14}$C—SCH 530348 (combined concentration 40 ng/μL, 5000 DPM/μL), SCH 540679 (40 ng/μL), and SCH 609528 (40 ng/μL)] into pooled pre-dose human plasma. The procedure resulted in 96.4% recovery of the added radiocarbon.

All available pooled plasma from SCH 530348 and placebo-dosed subjects was processed by solvent extraction by protein precipitation as described in the rising single dose study. Briefly, after extracting once with three volumes of acetonitrile, the supernatant was concentrated, then reconstituted in dimethyl sulfoxide (100-200 μL) followed by the addition of 111 mixture of mobile phases A and B (100-200 μL). A 100-μL-aliquot of each reconstituted extract was injected for LC-MS analysis. Targeted LC-MS/MS analysis to confirm the presence of metabolites was also performed. Table 5 provides the LC-MS response (by extracted ion chromatogram or "XIC") of metabolites detected in human plasma extracts relative to that of SCH 530348 following a multiple 28-day-oral administration of 5 mg of SCH 530348 to healthy subjects.

TABLE 5

| Drug/Metabolite Label | Name | $Rt^a$ (min) | m/z (Th) | Relative LC-MS Response (XIC) of SCH 530348 and Metabolites | | | | | | | |
|---|---|---|---|---|---|---|---|---|---|---|---|
| | | | | Day 1 | | Day 14 | | | Day 28 | | |
| | | | | $2^b$ | 6 | 0 | 2 | 6 | 0 | 2 | 6 |
| SCH 530348 | Parent Compound | 36.4 | 493 | 100 | 100 | 100 | 100 | 100 | 100 | 100 | 100 |
| M15 | Monooxy-SCH 530348 | 22.8 | 509 | $ND^c$ | ND | ND | ND | ND | ND | 0.22 | 0.40 |

TABLE 5-continued

| Drug/ Metabolite | | $Rt^a$ | m/z | Relative LC-MS Response (XIC) of SCH 530348 and Metabolites | | | | | | |
|---|---|---|---|---|---|---|---|---|---|---|
| | | | | Day 1 | | Day 14 | | | Day 28 | | |
| Label | Name | (min) | (Th) | $2^b$ | 6 | 0 | 2 | 6 | 0 | 2 | 6 |
| M16 | Carboxylic acid metabolite (SCH 609528) | 22.8 | 523 | ND | ND | ND | ND | $BIT^d$ | BIT | ND | BIT |
| M19 | Amine metabolite (SCH 540679) | 29.3 | 421 | ND | ND | ND | BIT | BIT | BIT | BIT | BIT |
| M20 | Monooxy-SCH 530348 | 30.4 | 509 | 0.44 | ND | 5.64 | 3.15 | 6.04 | 6.30 | 4.16 | 4.65 |
| M21 | Monooxy-SCH 530348 | 31.8 | 509 | ND | ND | 3.10 | BIT | 3.18 | 2.65 | 2.10 | 2.89 |

$^a$Retention time was obtained from LC-MS and LC-MS/MS experiments.
$^b$Collection time (hr)
$^c$ND = Not Detected
$^d$BIT = Below Integration Threshold Assuming that the extraction recovery and the LC-MS responses of SCH 530348 and its metabolites are similar, the parent compound (SCH 530348, m/z 493 Th) was the major drug-related component detected in plasma at all time points. On days 14 and 28, an increased LC-MS response from two monooxy metabolites (M20 and M21, m/z 509) was observed and ranged between 2-6.5% of LC-MS response for parent drug. Trace amounts of an amine (M19, SCH 540679, m/z 421 Th) and a carboxylic acid metabolite (M16, SCH 609528, m/z 523 Th) were detected on Days 14 and 28. An additional monooxy metabolite (M15, m/z 509) was detected in low amount on Day 28. All the metabolites detected in plasma samples after multiple dosing were previously detected in plasma and/or urine following single dose of SCH 530348. Structures of the administered drug and putative metabolites representing >0.2% of a LC-MS parent drug response are provided in FIG. 2.

Figure 2:
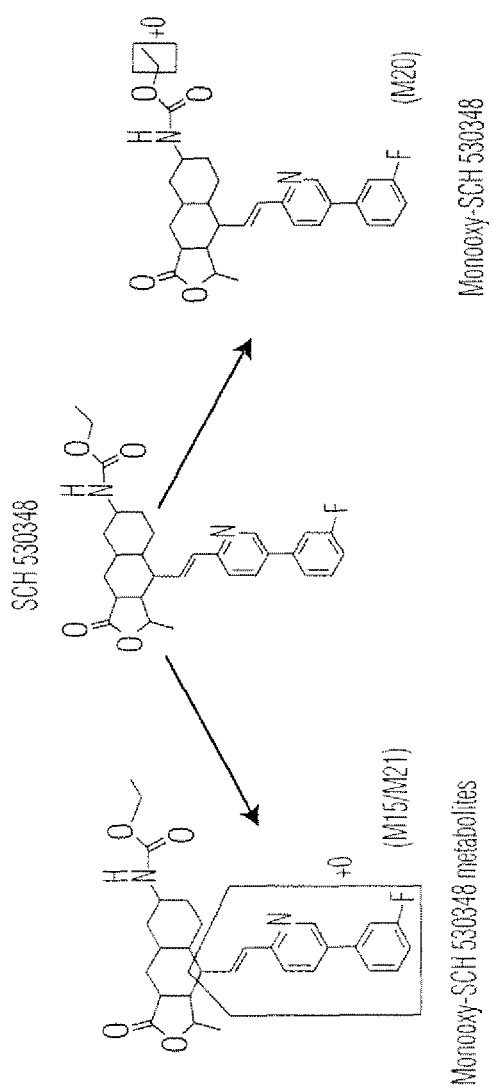
FIG. 2 illustrates the metabolites detected in human plasma representing >0.2% of LC-MS parent drug response following 5-mg administration of SCH 530348 for 28 days.

As summarized in FIG. 2, SCH 530348 metabolites, while only detected in minor to trace amounts, were mostly formed through monooxidation (M+16) at yet unknown positions.

The conclusions that can be drawn from the rising multiple dose study are as follows:

First, SCH 530348 was the predominant circulating drug-related component 1.0 detected on days 1, 14, and 28.

Second, compared to day 1, increases in relative amounts of M20 and M21 were detected on day 14, and no accumulation of other metabolites was observed.

Third, minor to trace level metabolites detected in human plasma were formed mostly through monooxidation at yet unknown positions.

Upon analysis, it was determined that, unlike the other detected metabolites, the concentration of the M20 metabolite in the blood was sufficient for it to be considered a "major metabolite." That finding triggered an evaluation of its activity. In order to assess activity, SCH 530348 and the M20 metabolite were subjected to a human coronary artery smooth muscle cell assay measuring effects on thrombin receptor agonist peptide TFLLRNPNDK-NH2 ("TK") on calcium efflux ("the calcium transient assay"). The resulting $IC_{50}$ values are 4.5 and 3.4 nM, respectively, The conclusion that the M20 metabolite qualified as an active major metabolite triggered further investigations into its structure and character, and it was given the designation of SCH 2046273.

Metabolite Characterization and Structures

Figure 3:
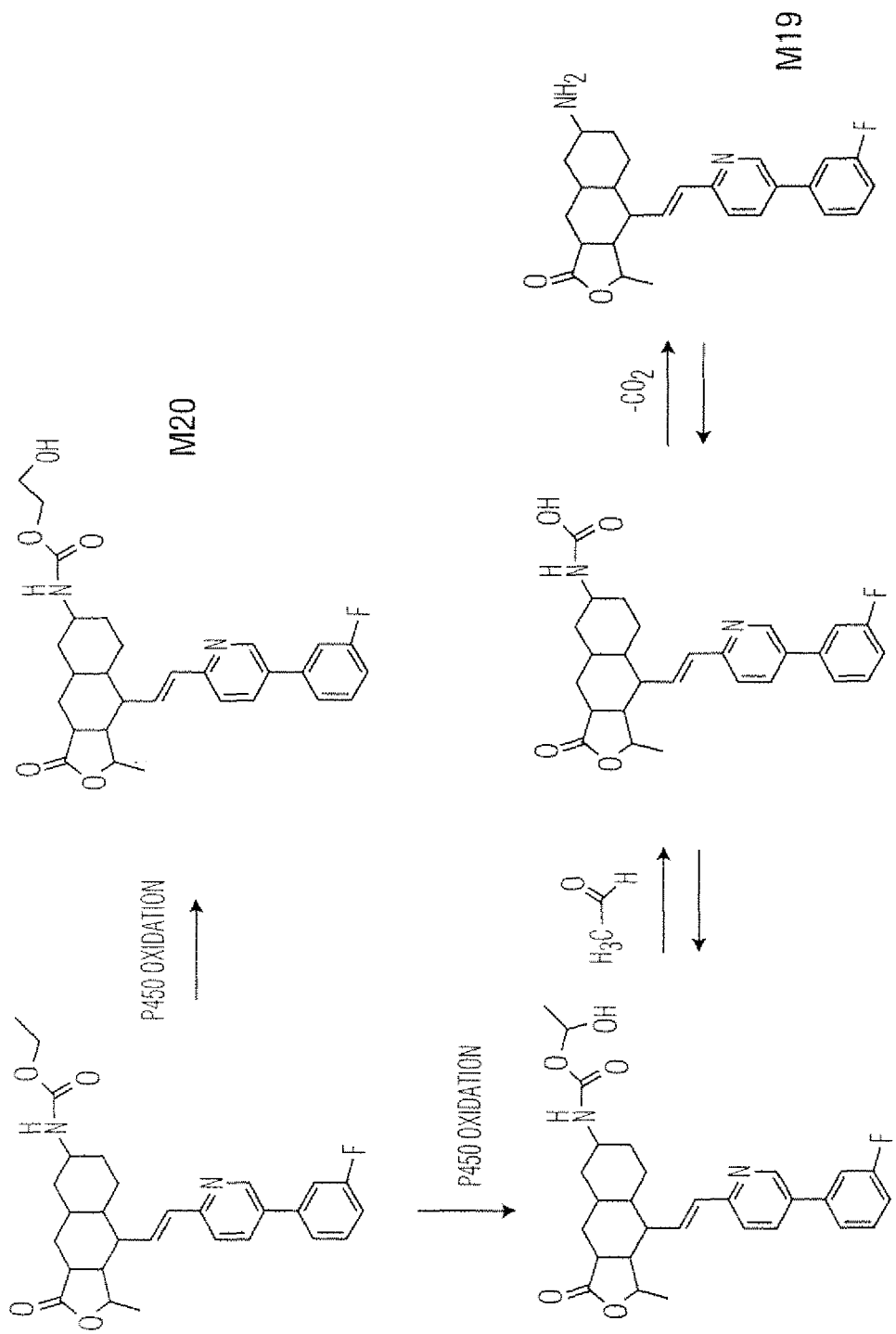
FIG. 3 illustrates the synthetic pathways from SCH 530348 to the M20 and M19 metabolites.
Figure 4:
FIG. 4 illustrates the mass spectrum ("MS") and MS-fragmented chemical structure of SCH 530348.
Figure 5:
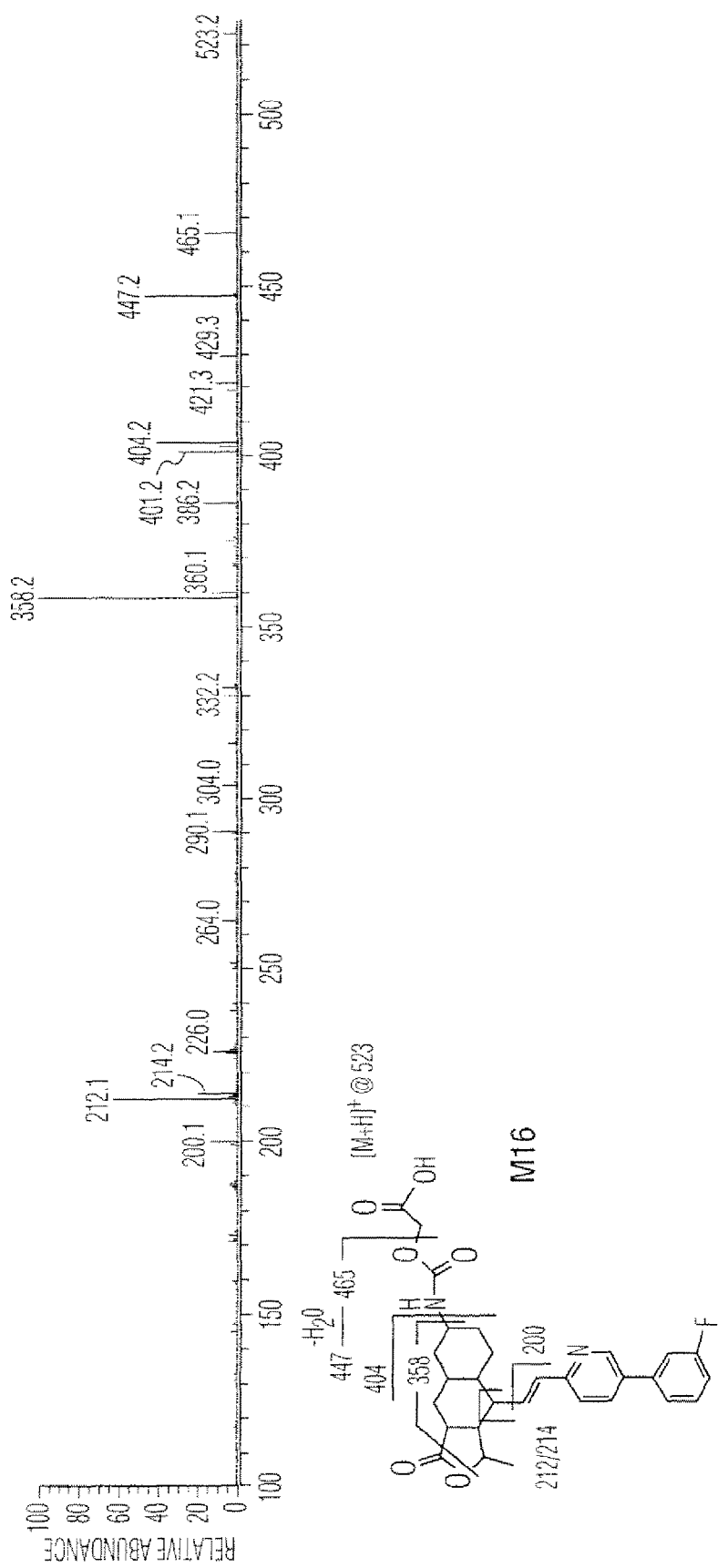
FIG. 5 illustrates the mass spectrum and MS-fragmented chemical structure of the M16 metabolite.
Figure 6:
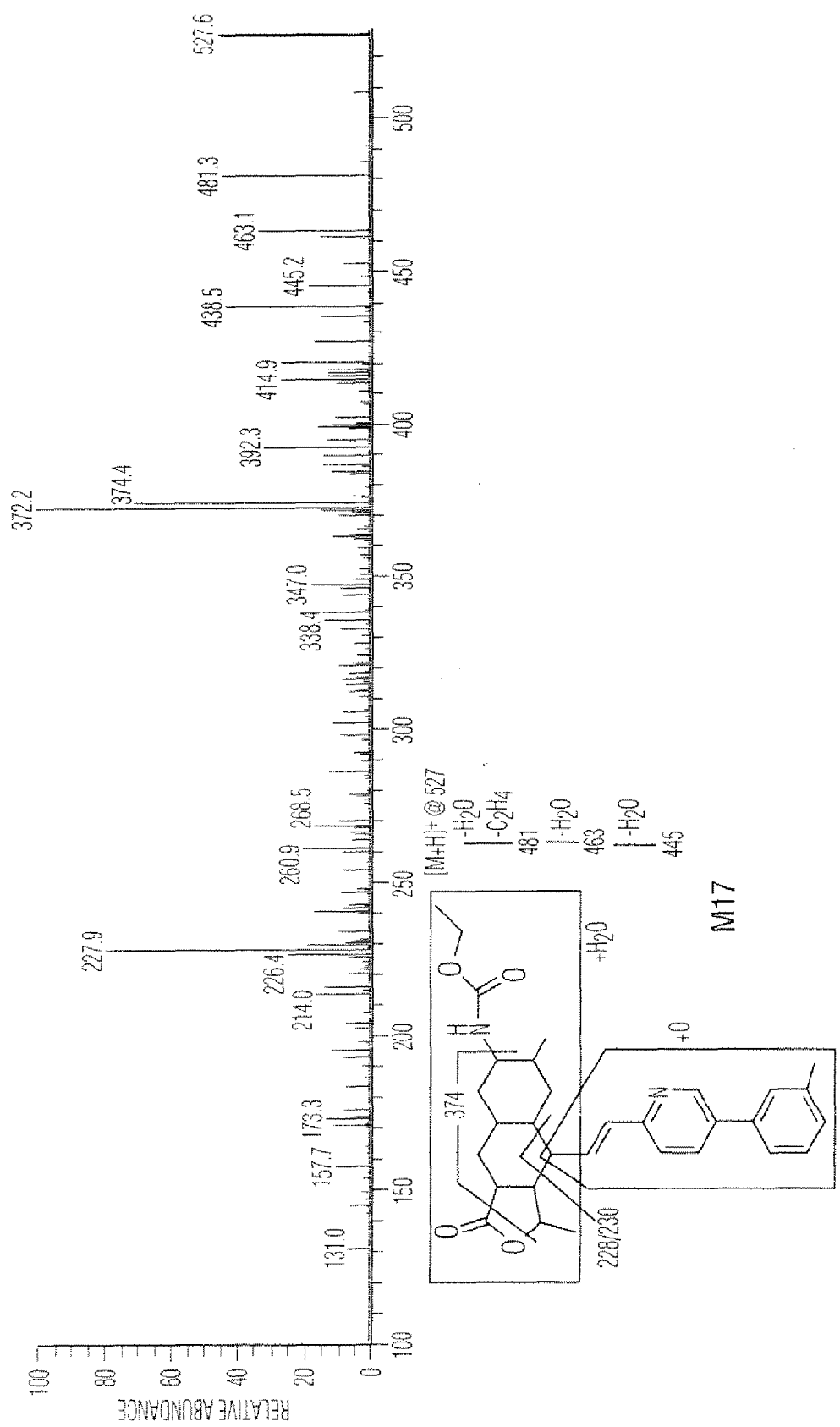
FIG. 6 illustrates the mass spectrum and MS-fragmented chemical structure of the M17 metabolite.
Figure 7:
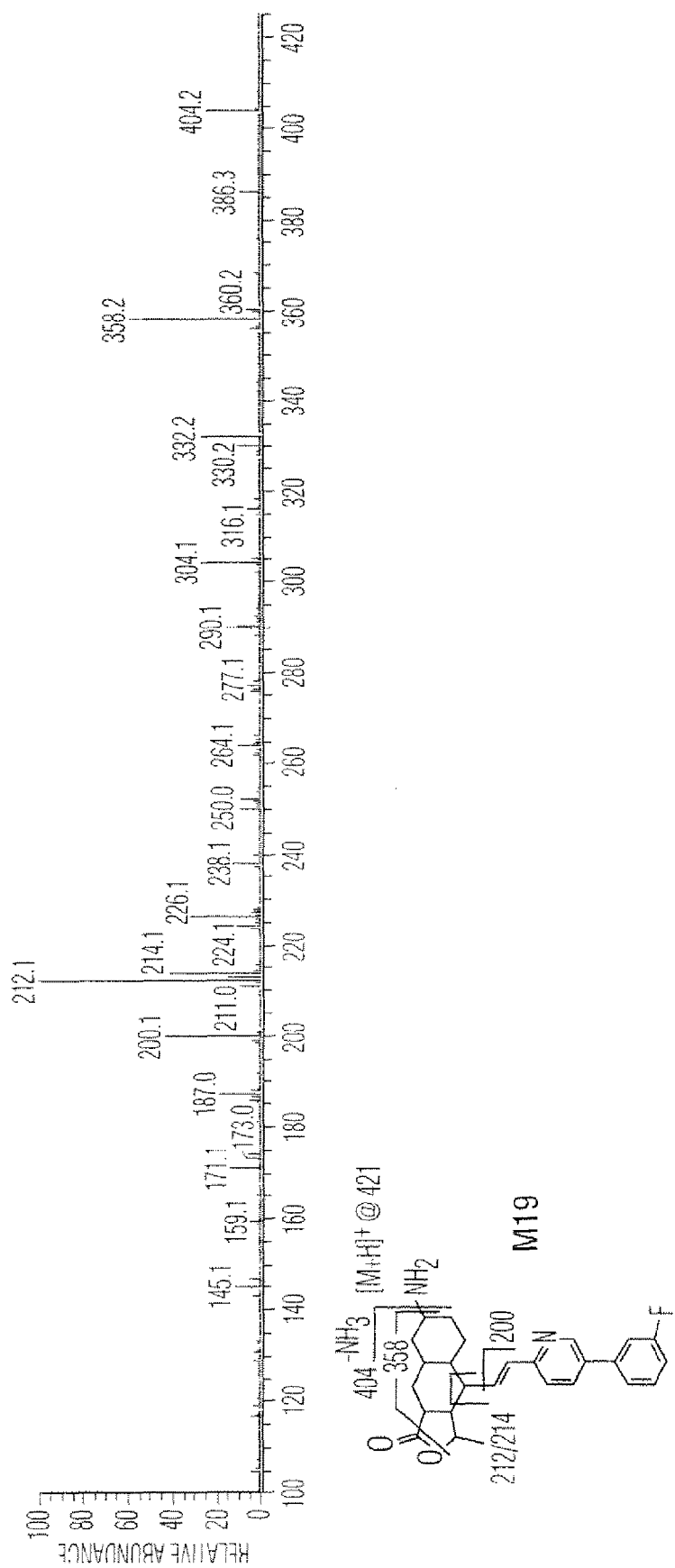
FIG. 7 illustrates the mass spectrum and MS-fragmented chemical structure of the M19 metabolite.
Figure 8:
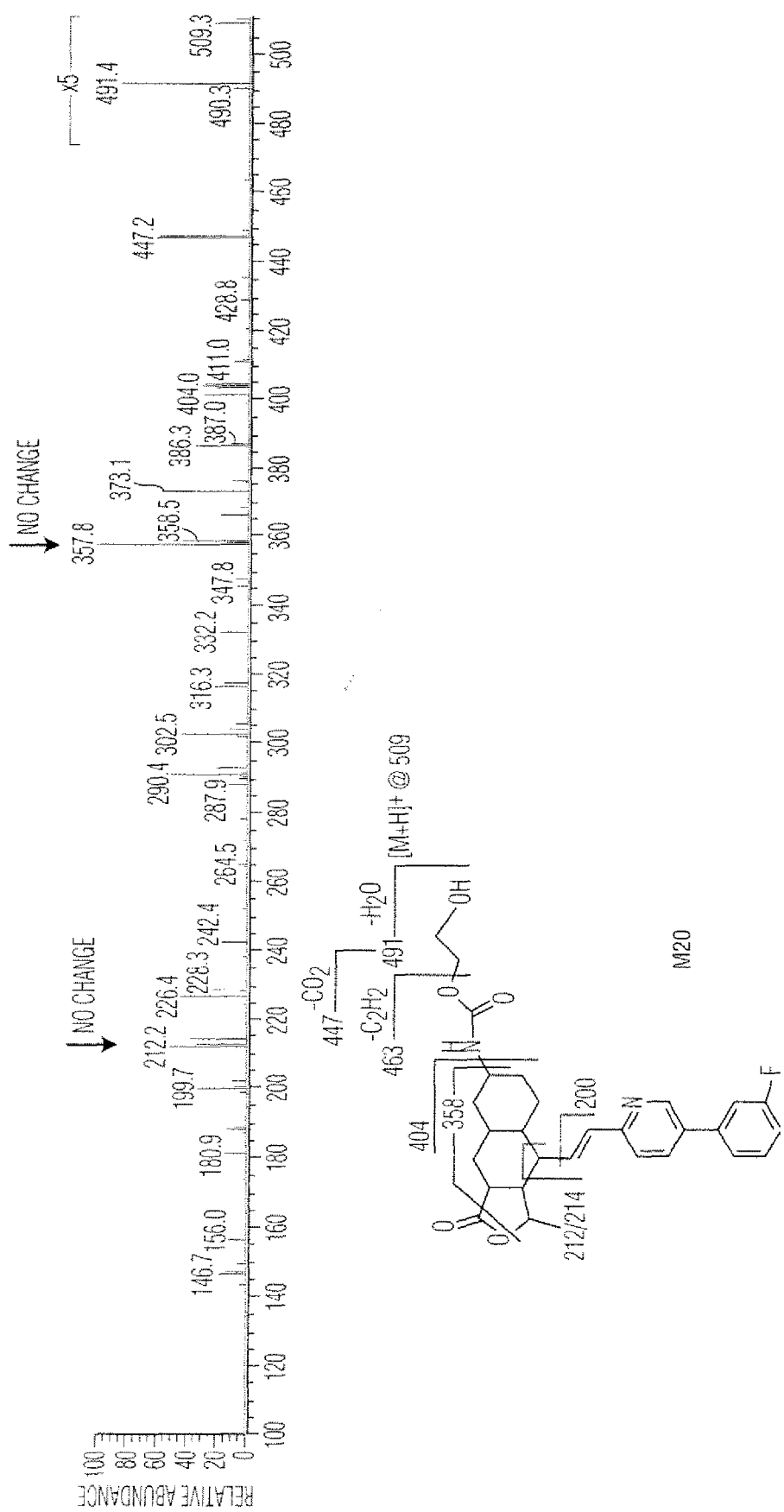
FIG. 8 illustrates the mass spectrum and MS-fragmented structure of the M20 metabolite.
Figure 9:
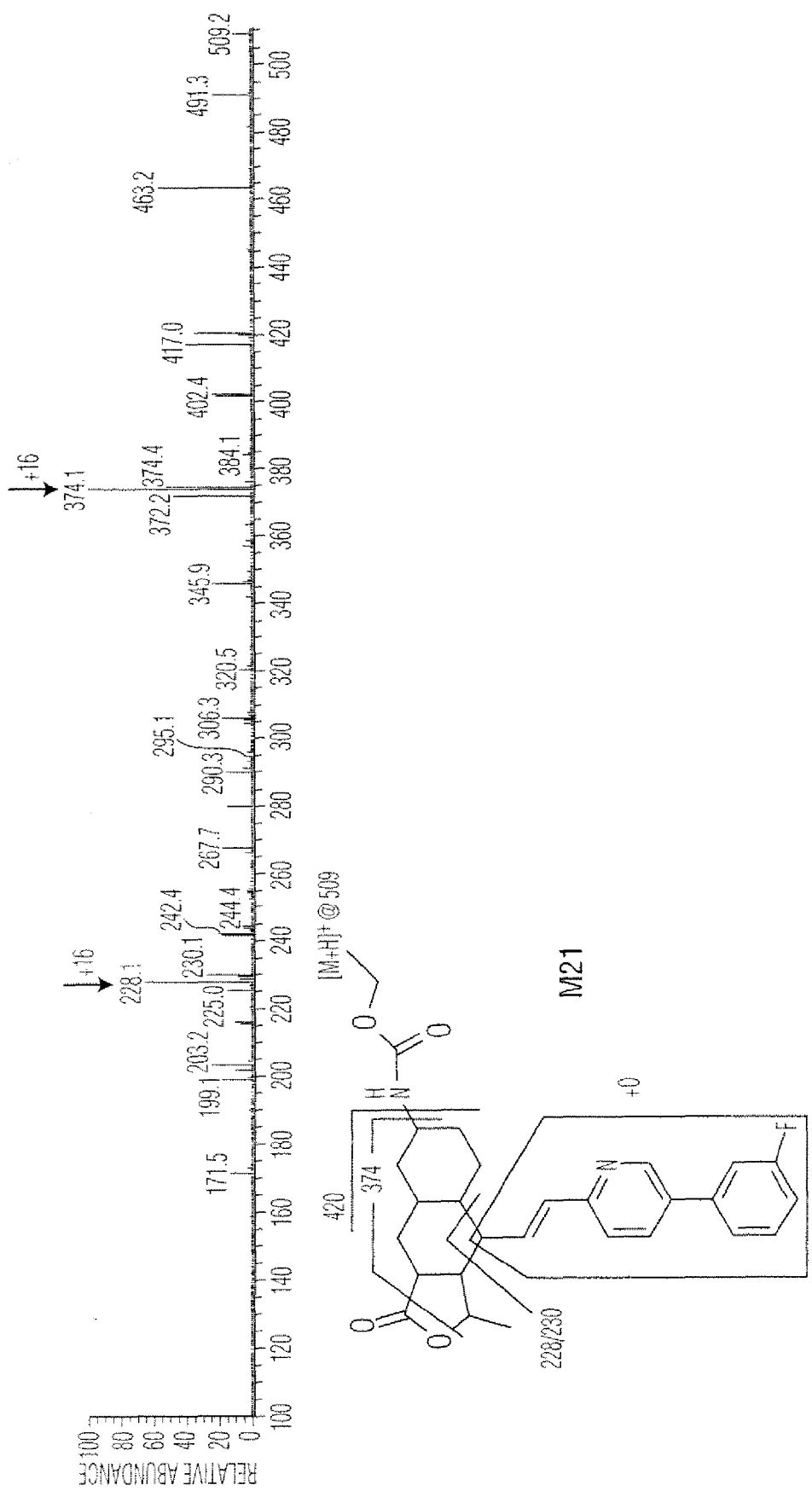
FIG. 9 illustrates the mass spectrum and MS-fragmented structure of the M21 metabolite.

Using the above described analytic methods, mass spectra of the isolated metabolites were generated. Using information from the mass spectra, chemical structures of the metabolites were inferred. FIG. 3 illustrates the synthetic pathways from SCH 530348 to the M20 and M19 metabolites. FIGS. 4-9 display the mass spectra and ms-fragmented chemical structures of SCH 530348 and the isolated metabolites labeled M16, M17, M19, M20 and M21, respectively.

Animal studies revealed that M20 is formed in rabbits after both single and multiple doses. Exposure multiples exceeded 10 in monkeys after a single dose at 0.5 mg/kg, 25 in mice after a single dose at 75 mg/kg, and 50 in female rabbits on day 7 after multiple daily doses at 20 mg/kg.

In a multi-center, randomized, double-blind, placebo-controlled study to evaluate the safety of SCH 530348 in subjects undergoing non-urgent percutaneous coronary intervention ("PCI"), blood samples were taken on days 15, 31, 60, 75, and 91. A steady state blood level concentration of SCH 530348 was reached by day 31. By day 31, the M20 metabolite was present in the blood at levels of 30-40% of those of the parent (SCH 530348).

Synthesis of SCH 2046273

SCH 2046273 was synthesized from SCH 500348W with triphosgene, ethylene gylcol and a copper(I) chloride catalyst according to the procedure of Miller (Miller, J. A.; Hennessy, E J.; Marshall, W. J.; Sciadone, M. A.; Nguyen, S. T., *J. Org. Chem.* 2003, 68, 7884-7886) to give the metabolite in an initial yield of 20% via a two-step reaction sequence. The low yield was due to side reactions involving the hydroxyl group of ethylene glycol. An improved procedure was developed to prepare a large quantity of SCH 2046273 using commercially available tetrahydropyranosyl-protected ethylene glycol in the reaction in place of ethylene glycol.

Facile deprotection can be achieved under mild conditions by pyridinium p-toluene sulfonate (PPTS). By careful monitoring of the intermediate isocyanate formation, to ensure completion had occurred, the overall yield was increased from 20% to 60% (see Example 1).

Other methods were also investigated to obviate the use of copper(I) chloride in the reaction, as on a large scale, it was difficult to remove the inorganic salts during work up. Instead of formation of an isocyanate (see Example 1), a process involving the direct reaction of SCH 500348W with chloroformate (4a) (derived from tetrahydropyranosyl-protected ethylene glycol) was considered (see Example 2). Additionally the reaction of SCH 530348 with ethylene carbonate (5a) to generate SCH 2046273 directly was attempted (see Example 3).

Although all three methods worked, the synthesis of Example 1 was chosen for the production of SCH 2046273, because of the ease of chromatographic separation of the final product.

Example 1

(3R,3aS,4S,4aR,7R,8aR)-7-amino-4{(E)-2-(5-(3-fluorophenyl)pyridine-2-yl)vinyl}-3methyldecahydronaphtho[2,3-c]furan-1(3H)-one (2)

To the 250 ml-round bottom flask that contained SCH 530348-W (1) (4.0 g, 8.12 mmol) was added a 2:1 mixture of conc. HCl:AcOH (80 mL). The resulting solution was heated at 118° C. for 16 h. The reaction mixture was then cooled to room temperature and concentrated to dryness to give a crude oil. The saturated $NaHCO_3$ solution was added into the crude oil to pH 8. The solution was then partitioned with $CH_2Cl_2$. The organic layer was separated and the aqueous layer was extracted with $CH_2Cl_2$(1×50 mL). The combined organic layers were dried over $Na_2SO_4$, and concentrated to dryness to give (2) as a white foam (3.4 g, 8.12 mmol, quantitative yield) without further purification.

Example 2

2-(tetrahydro-2H-pyran-2-yloxy)ethyl(1R,3aR,4aR,6R,8aR,9S,9aS)-9-{(E)-2-(5-(3-fluorophenyl)pyridine-2-yl)vinyl}-1-methyl-3-oxododecahydronaphtho[2,3-c]furan-6-ylcarbamate (4)

To the mixture of free amine (2) (2.30 g, 5.52 mmol) in $CH_2Cl_2$:sat.$NaHCO_3$:1:1 (56 mL) at 0° C. was added triphosgene (0.573 g, 1.93 mmol). The resulting solution was stirred at 0° C. for 30 min, then the organic layer was removed. The aqueous layer was extracted with $CH_2Cl_2$ (1×28 mL). The combined organic layers were then dried over $Na_2SO_4$ and concentrated to dryness to give the isocyanate intermediate as a clear foam. The clear foam was dissolved in anhydrous $CH_2Cl_2$ (70 mL) and copper(I) chloride (0.27 g, 2.76 mmol) was added. The resulting solution was stirred at room temperature for 10 minutes, followed by the addition of 2-(tetrahydro-2H-pyran-2-yloxy)ethanol (1.0 mL, 8.28 mmol). After stirring the reaction at 23° C. for 16 h, the reaction was washed with $H_2O$ (1×50 mL), dried over $Na_2SO_4$ and concentrated to dryness to give the blue crude oil (4). The product was then purified on Teledyne Isco 120 g Silica RediSep Rf column using a gradient of 0-3% MeOH in methylene chloride as eluent, to obtain the target compound 2.58 g, 80% yield.

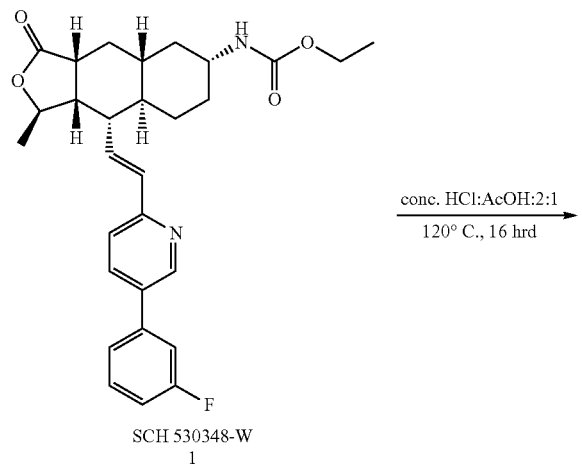

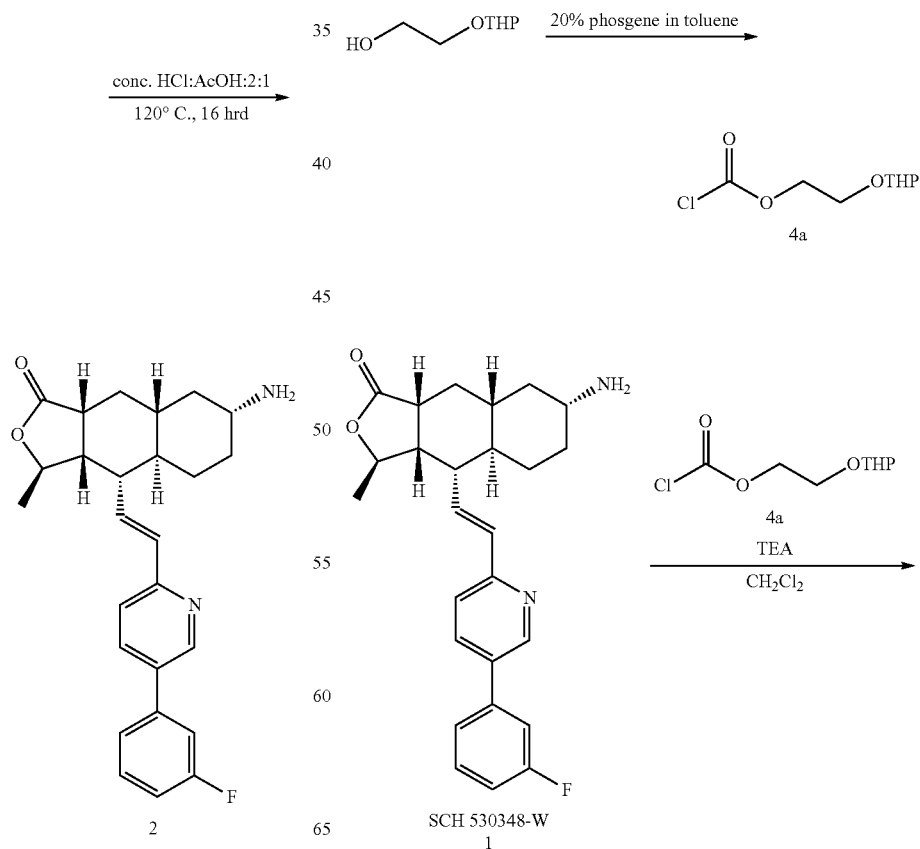

-continued

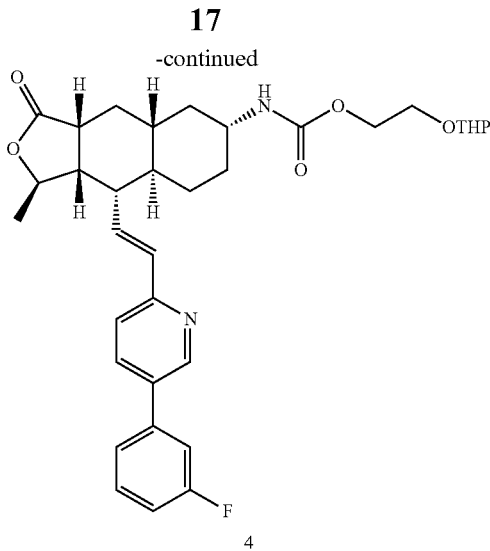

4

-continued

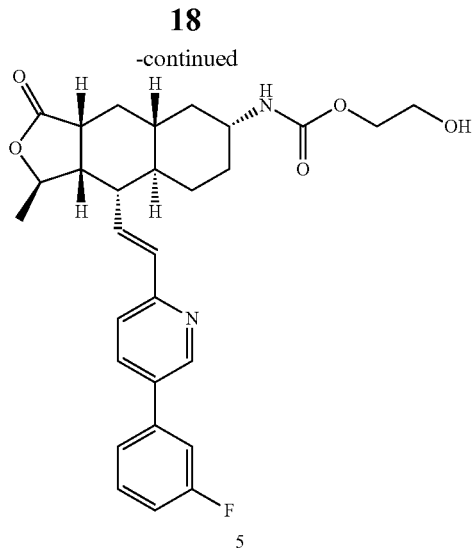

5

Example 3

2-hydroxyethyl(1R,3aR,4aR,6R,9S,9aS)-9-{(E)-2(5-(3-fluorophenyl)pyridine-2-yl)vinvl}-1-methyl-3-oxododecahydronaphtho[2,3-c]furan-6ylcarbamate. (5)

To a solution of compound (4) (2.49 g, 4.2 mmol) in absolute EtOH (74.5 mL), was added pyridinium p-toluenesulfonate (1.58 g, 6.3 mmol). The resulting solution was heated at 55° C. for 16 h. After the reaction was complete, the reaction was evaporated to dryness to give a crude clear oil (5). The product was then purified on Teledyne isco, 80 g Silica RediSep Rf flash column using a gradient of 0-5% MeOH in methylene chloride as eluent. A total of 1.70 g, 81% yield of pure white solid (5) was isolated at a chemical purity of 100% as determined by analytical HPLC (Supelco Ascentis Express C18, 50 mm×4.6 mm column, 320 nm. Mobile phase: 0.05 M aqueous triethylamine acetate pH 4:acetonitrile (60:40), isocratic for 5 minutes, followed by a step gradient to acetonitrile, 1.0 mL/min).

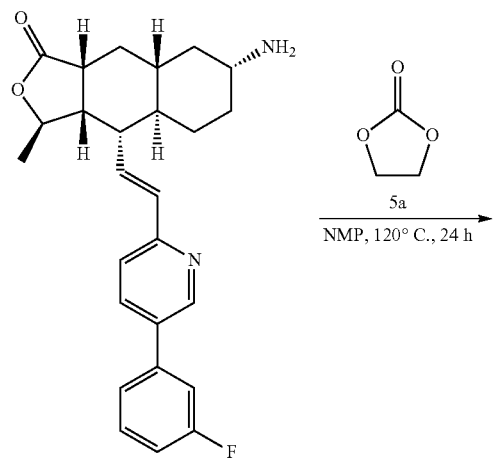

SCH 530348-W
1

Pharmaceutical Formulations

Pharmaceutical formulations of the M20 metabolite can be prepared using inert, pharmaceutically acceptable carriers in either solid or liquid form. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *The Science and Practice of Pharmacy*, 20th Edition, Lippincott Williams & Wilkins, Baltimore, Md., (2000).

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Immediate release tablet formulations of thrombin receptor antagonists, and of SCH 530348 in particular, are disclosed in U.S. application Ser. No. 11/771,520. This application discloses specific pharmaceutical formulations for both the 40 mg loading dose and the 2.5 mg maintenance dose, as well as broader ranges of formulations for each. Formulations of SCH 2046273 can be based on those for SCH 530348. Thus, examples of specific formulations of SCH 2046273 would include the following:

Loading Dose Formulation:

| Ingredient | Amount (mg) |
| --- | --- |
| SCK 2046273 | 40 |
| Lactose Monohydrate | 383 |
| Microcrystalline Cellulose | 120 |
| Croscarmellose Sodium | 36 |
| Povidone | 18 |
| Magnesium Stearate | 3 |

Maintenance Dose Formulation:

| Ingredient | Amount (mg) |
| --- | --- |
| SCH 2046273 | 2.5 |
| Lactose Monohydrate | 68 |
| Microcrystalline Cellulose | 20 |
| Croscarmellose Sodium | 6 |
| Povidone | 3 |
| Magnesium Stearate | 0.5 |

The formulations of the present invention are not limited to those exemplified above, or to those disclosed in the incorporated references. Any formulations that achieve the requirements of pharmaceutically acceptable drug product of M20 are within the inventors' scope of conception.

Indications

In some embodiments, the invention is directed to methods of treating acute coronary syndrome or peripheral arterial disease, or of treating a patient in need of secondary prevention by orally administering to a patient in need of such treating the pharmaceutical formulation.

Thrombin receptor antagonists are disclosed as being useful agents in the treatment of a variety of cardiovascular conditions in U.S. application Ser. No. 10/705,282. SCH 2046273 has similar utilities. Thus, among the cardiovascular conditions for which the SCH 2046273 is useful are the following: acute coronary syndrome, peripheral arterial disease, thrombosis, atherosclerosis, restenosis, hypertension, angina pectoris, arrhythmia, heart failure, myocardial infarction, glomerulonephritis, thrombotic stroke, thromboembolic stroke, and cerebral ischemia, deep vein thrombosis, venous thromboembolism, a cardiovascular disease associated with hormone replacement therapy, disseminated intravascular coagulation syndrome, renal ischemia, cerebral stroke, cerebral infarction, migraine, renal vascular homeostasis and erectile dysfunction.

"Secondary prevention" refers to the treatment of patients who have already suffered a significant cardiovascular event, such as a heart attack or stroke, to prevent another future, potentially more serious, perhaps lethal, cardiovascular or cerebrovascular event.

Thrombin receptor antagonists can be useful in the prevention of cardiovascular events associated with cardiopulmonary bypass surgery, as described in U.S. patent application Ser. No. 11/613,450. As an active thrombin receptor antagonist, SCH 2046273 may be a particularly effective agent in such use. Thus, the present invention is directed to a method of preventing a condition associated with coronary arterial bypass graft surgery comprising administering an effective amount of SCH 2046273 to a subject of said surgery. In some embodiments, the condition is selected from the group consisting of: bleeding; thrombotic vascular events such as thrombosis, restenosis; vein graft failure; artery graft failure; atherosclerosis, angina pectoris; myocardial ischemia; acute coronary syndrome myocardial infarction; heart failure; arrhythmia; hypertension; transient ischemic attack; cerebral function impairment; thromboembolic stroke; cerebral ischemia; cerebral infarction; thrombophlebitis; deep vein thrombosis; and, peripheral vascular disease.

The use of thombin receptor antagonists to control the risk of bleeding events in patients undergoing non-emergent percutaneous coronary intervention is disclosed in U.S. patent Ser. No. 12/051,504. Thus, within the scope of the present invention are methods of preventing a major cardiac event (e.g., myocardial infarction, urgent revascularization, or ischemia requiring hospitalization) in a patient who has undergone percutaneous coronary intervention comprising administering a therapeutically effective amount of SCH 2046273 to the patient. Also within the inventive scope are methods of inhibiting TRAP-induced platelet aggregation, which may or may not be associated with PCI.

As used above, and throughout this disclosure, the following terms, unless otherwise indicated, shall be understood to have the following meanings:

"Patient" includes both human and animals.

"Mammal" means humans and other mammalian animals.

Isolated and purified forms of the metabolites disclosed herein, including SCH 2046273, are within the scope of the present invention. The term "purified," "in purified form" or "in isolated and purified form" for a compound refers to the physical state of said compound after being isolated from a synthetic process (e.g., from a reaction mixture), or natural source or combination thereof. Thus, the term "purified," "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan. As examples, the purification techniques disclosed herein (e.g., LC-MS and LC-MS/MS techniques) result in isolated and purified forms of the subject metabolites. Such isolation and purification techniques would be expected to result in product purities of 95 wt % or better.

As used herein, the term "composition" is intended to encompass a product comprising the specified ingredients in the specified amounts, as well as any product which results, directly or indirectly, from combination of the specified ingredients in the specified amounts.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule is $H_2O$. Hydrates may occur as multiples or fractions of the active moiety. Thus, monohydrates, dihydrates, trihydrates and hemihydrates are nonlimiting examples of hydrates within the scope of the present invention.

One or more compounds of the invention may optionally be converted to a solvate. Preparation of solvates is generally known. Thus, for example, M. Caira et al, *J. Pharmaceutical Sci.,* 93(3), 601-611 (2004) describes the preparation of the solvates of the antifungal fluconazole in ethyl acetate as well as from water. Similar preparations of solvates, hemisolvate, hydrates and the like are described by E. C. van Tonder et al, *AAPS PharmSciTech.,* 5(1), article 12 (2004); and A. L. Bingham et al., *Chem. Commun.,* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example, I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

SCH 2046273 can form salts which are also within the scope of this invention. Reference to SCH 2046273 herein is understood to include reference to salts thereof, unless otherwise indicated. The term "salt(s)," as employed herein, denotes acidic salts formed with inorganic and/or organic acids, as well as basic salts formed with inorganic and/or organic bases. Zwitterions ("inner salts") are included within the term "salt(s)" as used herein. Pharmaceutically acceptable (i.e., non-toxic, physiologically acceptable) salts are preferred, although other salts are also useful. Salts of SCH 2046273 may be formed, for example, by reacting SCH 2046273 with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention. The free base of SCH 2046273 is also within the scope of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of SCH 2046273, and salts, solvates, and esters thereof, may exist in their tautomeric form (for example, as an amide or imino ether). All such tautomeric forms are contemplated herein as part of the present invention.

SCH 2046273 contains asymmetric or chiral centers, and, therefore, may exist in different stereoisomeric forms. It is intended that all stereoisomeric forms of SCH 2046273, as well as mixtures thereof, including racemic mixtures, form part of the present invention. In addition, the present invention embraces all geometric and positional isomers. For example, both the cis- and trans-forms of SCH 2046273, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Atropisomers (e.g., substituted biaryls) of SCH 2046273 are considered as part of this invention. Enantiomers can also be separated by use of chiral HPLC column.

All tautomeric forms of SCH 2046273 are embraced within the scope of the invention. Also, for example, all keto-enol and imine-enamine forms of SCH 2046273 are included in the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt," "solvate," "ester," and the like, is intended to equally apply to the salt, solvate, and ester of enantiomers, stereoisomers, rotamers, tautomers, positional isomers, and racemates of SCH 2046273.

The present invention also embraces isotopically-labelled compounds of SCH 2046273, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of SCH 2046273 (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of SCH 2046273 can generally be prepared by following procedures analogous to those disclosed in the Schemes and/or in the Examples hereinbelow, by substituting an appropriate isotopically labelled reagent for a non-isotopically labelled reagent.

Crystalline forms of SCH 2046273, and of the salts, solvates, and esters of the compounds of SCH 2046273, are intended to be included in the present invention.

Dosing regimens that have been considered for commercialization of SCH 530348 include loading doses of 10, 20 and 40 mg and maintenance doses of 0.5, 1, 2.5 and 5 mg, in solid, immediate-release tablet formulations for oral administration. Similar dosing regimens of SCH 2046273 are within the scope of the present invention. The current phase III clinical trials of SCH 530348 for ACS include a dosing regimen of a 40 mg loading dose followed by a once daily maintenance dose of 2.5 mg. Rapidly dissolving dosage forms, including lyophilized and effervescent dosage forms, are also within the scope of the invention.

The above description is not intended to detail all modifications and variations of the invention. It will be appreciated by those skilled in the art that changes can be made to the embodiments described above without departing from the inventive concept. It is understood, therefore, that the invention is not limited to the particular embodiments described above, but is intended to cover modifications that are within the spirit and scope of the invention, as defined by the language of the following claims.

What is claimed is:

1. A compound of the following formula:

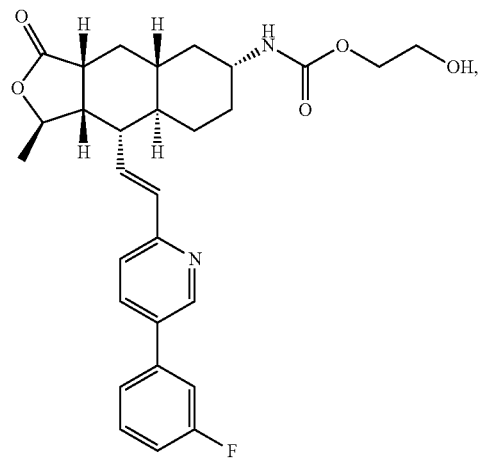

or a pharmaceutically acceptable salt or hydrate thereof in an isolated or purified form.

2. The free base of the compound according to claim 1.
3. A pharmaceutically acceptable salt of the compound according to claim 1.
4. A hydrate form of the compound according to claim 1.
5. A pharmaceutical composition comprising an effective amount of a compound of the formula

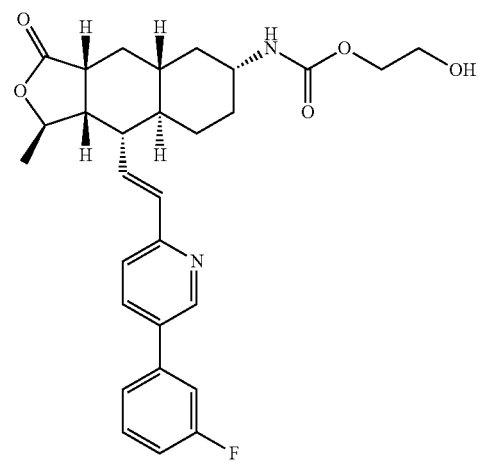 [SMILES: C[C@H]1OC(=O)[C@@H]2C[C@@H]3C[C@H](NC(=O)OCCO)CC[C@H]3[C@H](/C=C/c3ccc(-c4cccc(F)c4)cn3)[C@H]12]

or a pharmaceutically acceptable salt or hydrate thereof, and a pharmaceutically acceptable carrier.

6. The pharmaceutical composition according to claim 5, which further comprises one or more additional cardiovascular agents.
7. The pharmaceutical composition according to claim 6, wherein said cardiovascular agent is aspirin, clopidogrel, prasugrel, or the pharmaceutically acceptable salts hydrates of said agents.

* * * * *